United States Patent [19]

Dolovich et al.

[11] Patent Number: 5,762,943
[45] Date of Patent: Jun. 9, 1998

[54] METHODS OF TREATING TYPE I HYPERSENSITIVITY USING MONOPHOSPHORYL LIPID A

[75] Inventors: Jerry Dolovich, Hamilton, Canada; J. Terry Ulrich, Corvallis, Mont.; Jean S. Marshall, Etobicoke, Canada

[73] Assignee: Ribi ImmunoChem Research, Inc., Hamilton, Mont.

[21] Appl. No.: 645,672

[22] Filed: May 14, 1996

[51] Int. Cl.⁶ .................. A61K 39/35; A61K 45/00; A61K 39/02
[52] U.S. Cl. .................. 424/275.1; 424/275.1; 424/283.1; 424/282.1; 424/234.1; 424/257.1; 424/197.1; 424/422; 424/418; 424/182; 424/177; 424/195; 424/400; 424/450; 424/70.13; 514/54; 514/960; 514/2; 530/329; 536/5; 536/124
[58] Field of Search .................. 424/422, 418, 424/182, 177, 195, 400, 450, 70.13, 234.1, 275.1, 257.1, 197.1, 282.1, 283.1; 536/5, 124; 514/960, 920, 54; 530/329

[56] References Cited

U.S. PATENT DOCUMENTS

| | | |
|---|---|---|
| 4,432,969 | 2/1984 | Batchelor . |
| 4,436,727 | 3/1984 | Ribi . |
| 4,844,894 | 7/1989 | Ribi . |
| 4,912,094 | 3/1990 | Myers et al. . |
| 4,990,336 | 2/1991 | Silvestri et al. . |
| 5,013,555 | 5/1991 | Collins . |
| 5,073,628 | 12/1991 | Matsuhashi et al. . |
| 5,244,663 | 9/1993 | Bruttmann et al. . |

FOREIGN PATENT DOCUMENTS

| | | |
|---|---|---|
| 9312778 | 7/1993 | WIPO . |
| 9315766 | 8/1993 | WIPO . |

*Primary Examiner*—Paula K. Hutzell
*Assistant Examiner*—Khalid Masood
*Attorney, Agent, or Firm*—Ronald H. Kullick

[57] ABSTRACT

Methods and compositions for treating type I immunoglobin E (IgE)-dependent hypersensitivity by the administration of monophosphoryl lipid A (MLA) or 3-deacylated monophosphoryl lipid A (3D-MLA) are disclosed. MLA or 3D-MLA administered alone or in combination with an allergen to a patient suffering from type I hypersensitivity reduces levels of total or allergen specific IgE and increases levels of IgG antibody in that patient. MLA and 3D-MLA can be administered as part of a desensitization regimen or as a component of a prophylactic vaccine to prevent a type I hypersensitivity reaction.

17 Claims, No Drawings

5,762,943

1

METHODS OF TREATING TYPE I HYPERSENSITIVITY USING MONOPHOSPHORYL LIPID A

TECHNICAL FIELD

This invention relates to methods of treating or preventing type I immunoglobulin E (IgE) dependent hypersensitivity by the administration to a patient of monophosphoryl lipid A or 3-deacylated monophosphoryl lipid A alone or in combination with an allergen.

BACKGROUND OF THE INVENTION

Type I IgE-dependent hypersensitivity, typified by atopic allergy reactions, occurs in certain individuals who overproduce IgE antibodies upon exposure to environmental antigens (allergens). Allergies afflict substantial numbers of people worldwide, including over 40 million in the United States. Allergic diseases include rhinitis, asthma and atopic dermatitis. Common environmental allergens include pollens, molds, foods, drugs, house dust mites and animal dander.

There has been a considerable increase in the understanding of the immune mechanisms underlying a type I IgE-dependent hypersensitive response in recent years. The molecular basis for type I hypersensitivity involves complex interactions of several branches of the immune system. These complex interactions in the allergy cascade provide many possible points for therapeutic intervention. It is generally understood that type I hypersensitivity results from formation of allergen-specific IgE. The allergen-specific IgE binds passively to mast cells in the tissues or basophils which are mainly in the blood. The onset of the allergic reaction is initiated by exposure topically, by injection, by ingestion or by inhalation to the allergen which binds to the IgE on the mast cells or basophils, and possibly other cells, causing the cells to release a large number of mediators, including histamine. These mediators cause a variety of clinical manifestations such as asthma, edema and inflammation. In certain individuals symptoms may be particularly severe, resulting in anaphylactic shock and possibly death if treatment is not immediate. Clinical symptoms are most often treated with a variety of drugs, including antihistamines, cromolyn and adrenocortical steroids.

Allergen immunotherapy in the form of a desensitization regimen is also widely used for treatment of individuals afflicted with clinically significant type I hypersensitivity reactions. Over a period of time, the individual is inoculated with small amounts of the offending allergen in an effort to achieve clinical hypo-responsiveness or desensitization against the allergen. Typically, the initial dose of the allergen is very low and gradually increases to a so-called maintenance dose which may be continued for months or years. While this type of immunotherapy has become commonplace for the treatment of sufferers from atopic allergies (including hay fever, insect sting allergy and some forms of asthma), it has significant disadvantages. Of greatest concern is the risk of a severe allergic reaction from the administration of the allergen. This inherent risk of a severe allergic reaction, such as anaphylactic shock, dictates that the treatment regimen initially employ very low amounts of allergen and only gradually increase the dose of allergen, thus prolonging the length of treatment and increasing the number of injections necessary to achieve satisfactory results since results with the treatment as now used are dose-dependent. Thus, the overall success of immunotherapy has been limited, and clinical management often focuses on control of symptoms with medications, rather than modulation of the allergy cascade by immunologic methods such as allergen immunotherapy. In addition, in patients with persistent allergic reactions, desensitization procedures are often employed with mixed results. Allergen immunotherapy elicits complex immunological responses, including the stimulation of blocking antibodies (mainly IgG) which neutralize the allergen, the alteration of the host response from a $TH_2$ to more of a $TH_1$ response, the stimulation of an initial rise and then gradual decrease in IgE antibodies to the specific allergen injected, the stimulation of specific anti-idiotypic antibodies, and a decrease in the allergic-type inflammatory response.

In an effort to reduce the negative aspects of immunotherapy while preserving or enhancing its benefits, a variety of alternative therapeutic approaches have been considered. These alternative approaches include reformulating the allergen which is administered to the individual afflicted with a type 1 hypersensitivity reaction. Such formulations include alum precipitated allergen extracts, chemically modified allergen preparations, allergen entrapped within liposomes, and allergen used in conjunction with other adjuvants. U.S. Pat. No. 5,013,555 describes the use of liposomes containing allergen. U.S. Pat. No. 4,990,336 describes a multiphasic sustained release delivery system that employs microcapsules. Oral therapy in which the allergen is administered in a solid support is described in U.S. Pat. No. 5,244,663. Alum is currently the only adjuvant approved by the United States Food and Drug Administration (FDA). However, in animal models, alum has been demonstrated to enhance IgE production rather than reduce it, which is undesirable. Other adjuvants such as saponin (U.S. Pat. No. 4,432,969) and an alkyl ester of tyrosine for use in desensitization therapy have also been described. Other treatment approaches include modified peptides (U.S. Pat. No. 5,073,628) or IL-4 receptor antagonists (PCT WO 93/15766). These alternative approaches have potential limitations such as the lack of allergen specificity or a risk of eliciting unacceptable reactions. Although specific allergen immunotherapy has proved effective to some extent, it is not consistently safe or successful for all patients or all allergens. As presently used, allergen immunotherapy remains a controversial form of therapy. There is a continued need for alternative or complimentary, effective strategies of allergy therapy.

SUMMARY OF THE INVENTION

The present invention is directed to a method of treating or preventing type I IgE-dependent hypersensitivity in individuals and compositions for such treatment. The method comprises administering to the individual an effective amount of monophosphoryl lipid A (MLA) or 3-deacylated monophosphoryl lipid A (3D-MLA). It has been surprisingly discovered that MLA or 3D-MLA administered to an individual afflicted with type I hypersensitivity reduces total or allergen-specific IgE while favorably inducing the production of IgG antibodies. IgG antibodies are blocking antibodies which reduce allergic reactions. MLA or 3D-MLA may be dispensed in an effective amount in a suitable vehicle in accordance with a suitable regimen alone or administered with an allergen as part of an allergen-specific type I hypersensitivity desensitization regimen. These compounds may also be added to a vaccine composition to elicit benefits in terms of IgE-dependent allergy as well as enhance the vaccine effect. The administration of MLA or 3D-MLA results in a reduced risk of potentially serious and even fatal allergic reactions in hypersensitive individuals upon exposure to an allergen(s) to which the individual is hypersensitive.

The invention also includes pharmaceutical compositions for the treatment of type I hypersensitivity comprising an effective amount of MLA or 3D-MLA in a suitable vehicle alone or in combination with an allergen or mixture of allergens. Alternatively, MLA or 3D-MLA may be administered sequentially with, but separate from, the allergen or allergen mixture.

DETAILED DESCRIPTION OF THE INVENTION

It has been discovered that the administration of MLA or 3D-MLA to individuals afflicted with type I hypersensitivity modulates the allergic response to given allergens to which the individual has sensitivity.

A type I hypersensitive reaction ranging from a relatively minor reaction eliciting symptoms like those most often observed with what is commonly referred to as "hay fever," to a severe reaction such as anaphylactic shock, which can result in death, is initiated by pharmacologically active materials including histamine, which are released in the body. These materials are released from mast cells and other cells after allergen binds to an antibody from what is known as the IgE class which is fixed to the mast cells, basophils and possibly other cells. It has been observed that individuals having type I hypersensitivity possess an abnormally high amount of IgE antibody to substances such as ragweed pollen, cat dander, house dust mites or other substances that cause their allergic reactions or diseases.

It has been discovered that the administration of MLA or 3D-MLA in an effective amount dispensed in a suitable vehicle substantially reduces the titer of IgE class antibodies, thereby reducing the amount of IgE antibody available to attach to mast cells which effectively reduces the release of histamine and other mediators. While not being bound to any specific theory, it is believed that the administration of MLA or 3D-MLA may stimulate the elaboration of allergen-specific IgG and reduce the elaboration of IgE antibody. The IgG would then bind and neutralize the allergen, essentially blocking the IgE-allergen interaction which initiates the hypersensitivity reaction. The reduced IgE lowers the tendency for the individual to have an allergic reaction from the allergen.

The present invention provides an improved alternative over existing therapies in that, depending upon the patient, administration of a pharmaceutical composition containing an effective amount of MLA or 3D-MLA may preferably stimulate IgG antibody over IgE antibody, thereby substantially diminishing the allergic response to a given allergen(s) without the need for the administration of allergen as part of a desensitization regimen. In cases where a desensitization regimen is used involving co-administration of a pharmaceutical composition containing an effective amount of MLA or 3D-MLA with the appropriate allergen(s), the method could diminish the risk of an allergic reaction to the administration of the allergen(s). This would be accomplished by the possibility of the present invention to permit a change in allergen immunotherapy wherein smaller amounts of desensitizing allergen or smaller number of injections are required.

Effective amounts of MLA or 3D-MLA administered with a bacterial vaccine would likewise cause a reduction in total IgE while promoting the production of IgG. The IgG produced would be specific to the bacterial antigen in the vaccine enhancing the vaccine's effect. Vaccines prepared for the primary immunization of infants, which is a normal procedure in infancy to prevent infections, containing MLA or 3D-MLA could reduce the tendency of the infant to become allergic to the wide variety of allergens in the environment.

As used herein, "treatment" of type I hypersensitivity is an approach for obtaining beneficial or desired clinical results. Desired clinical results include, but are not limited to, the prevention of the onset of or alleviation of symptoms.

In accordance with the present invention the active compound for treating individuals suffering from type I hypersensitivity is a refined detoxified endotoxin selected from the group consisting of monophosphoryl lipid A (MLA) and 3-deacylated monophosphoryl lipid A (3D-MLA). Both MLA and 3D-MLA are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 4,912,094 to Myers, et al., also assigned to Ribi ImmunoChem Research, Inc., embodies 3-deacylated monophosphoryl lipid A and a method for its manufacture. Disclosures of each of these patents with respect to MLA and 3D-MLA are incorporated herein by reference.

Without going into the details of the prior incorporated by reference patents, monophosphoryl lipid A (MLA) as used herein is derived from lipid A, a component of enterobacterial lipopolysaccharides (LPS), a potent but highly toxic immune system modulator.

Edgar Ribi and his associates achieved the production of monophosphoryl lipid A (MLA) referred to originally as refined detoxified endotoxin (RDE). MLA is produced by refluxing an endotoxin extract (LPS or lipid A) obtained from heptoseless mutants of gram-negative bacteria in mineral acid solutions of moderate strength (0.1N HCl) for a period of approximately 30 minutes. This treatment results in the loss of the phosphate moiety at position 1 of the reducing end glucosamine.

Coincidentally, the core carbohydrate is removed from the 6 position of the nonreducing glucosamine during this treatment. The resulting product (MLA) exhibits considerable attenuated levels of the endotoxic activities normally associated with the endotoxin starting material, such as pyrogenicity, local Shwarzman reactivity, and toxicity as evaluated in the chick embryo 50% lethal dose assay ($CELD_{50}$). However, it unexpectedly retains the functionality of lipid A and LPS as an immunomodulator.

Another detoxified endotoxin which may be utilized in the practice of the present invention is referred to as 3-deacylated monophosphoryl lipid A (3D-MLA). 3D-MLA is known as set forth in U.S. Pat. No. 4,912,094, reexamination certificate B1 4,912,094, and differs from MLA in that there is selectively removed from the MLA molecule the B-hydroxymyristic acyl residue that is ester linked to the reducing-end glucosamine at position 3 under conditions that do not adversely affect other groups. 3-deacylated monophosphoryl lipid A is available from Ribi ImmunoChem Research, Inc., Hamilton, Mont. 59840.

The MLA and 3D-MLA molecules are a composite or mixture of a number of fatty acid substitution patterns, i.e., heptaacyl, hexaacyl, pentaacyl, etc., with varying fatty acid chain lengths. Thus, various forms of MLA and 3D-MLA, including mixtures thereof, are encompassed by this invention. The lipid A backbone that is illustrated in the –094 patent corresponds to the product that is obtained by 3-deacylation of heptaacyl lipid A from *S. minnesota* R595. Other fatty acid substitution patterns are encompassed by this disclosure; the essential feature is that the material be 3-deacylated.

The modified 3D-MLA utilized in the present invention is prepared by subjecting MLA to alkaline hydrolysis under conditions that result in the loss of but a single fatty acid from position 3 of the lipid A bat bone. B-hydroxymyristic fatty acid at position 3 is unusually labile in alkaline media. It requires only very mild alkaline treatment to completely 3-deacylate lipid A. The other ester linkages in lipid A require somewhat stronger conditions before hydrolysis will occur so that it is possible to selectively deacylate these materials at position 3 without significantly affecting the rest of the molecule. The reason for the unusual sensitivity to alkaline media of the ester-linked B-hydroxymyristic fatty acid at position 3 is not known at this time.

Although alkaline hydrolysis procedures are known, it is important to choose conditions that do not cause further hydrolysis beyond the ester linkage to the B-hydroxymyristic at position 3.

In general the hydrolysis can be carried out in aqueous or organic media. In the latter case, solvents include methanol (alcohols), dimethyl sulfoxide (DMSO), dimethylformanide (DMF), chloroform, dichloromethane, and the like, as well as mixtures thereof. Combinations of water and one or more of the mentioned organic solvents also can be employed.

The alkaline base can be chosen from among various hydroxides, carbonates, phosphates and amines. Illustrative bases include the inorganic bases such as sodium hydroxide, potassium hydroxide, sodium carbonate, potassium carbonate, sodium bicarbonate, potassium bicarbonate, and the like, and organic bases such as alkyl amines, and include, but are not limited to, diethylamine, triethylamine, and the like.

In aqueous media the pH is typically between approximately 10 and 14 with a pH of about 12 to about 13.5 being the preferred range. The hydrolysis reaction is typically carried out at a temperature of from about 20° C. to about 80° C., preferably about 50° C. to 60° C. for a period of about 10 to about 30 minutes. For example, the hydrolysis can be conducted in 3% triethylamine in water at room temperature (22°–25° C.) for a period of 48 hours. The only requirement in the choice of temperature and time of hydrolysis is that deacylation occurs to remove only the B-hydroxymyristic at position 3.

In practice it has been found that a particularly desirable hydrolysis method involves dissolving lipid A or monophosphoryl lipid A in chloroform:methanol 2:1 (v/v), saturating this solution with an aqueous buffer consisting of 0.5M $Na_2CO_3$ at pH 10.5, and then to flash evaporate the solvent at 45°–50° C. under a vacuum for an aspirator (approximately 100 mm Hg). The resulting material is selectively deacylated at position 3. This process can also be carried out with any of the inorganic bases listed above. The addition of a phase transfer catalyst, such as tetrabutyl ammonium bromide, to the organic solution prior to saturating with the aqueous buffer may be desirable in some cases. In addition to MLA and 3D-MLA produced as described above, MLA and 3D-MLA produced by synthetic or semi-synthetic processes may be used.

It has been observed that MLA or 3D-MLA when administered to warm blooded animals at safe, effective doses, reduces the level of IgE antibody, thereby reducing the risk for serious allergic response to exposure to an allergen(s).

The method of the present invention embodies the administration to warm blooded animals, preferably humans, of a pharmacologically effective amount of a composition comprising a detoxified endotoxin selected from the group consisting of MLA and 3D-MLA with a pharmaceutically effective carrier. As used herein, the term pharmaceutically effective amount means the amount of the composition that is sufficient to elicit a demonstrable patient response, i.e., reduce the total amount of IgE antibody and/or increase the total amount of IgG antibody to achieve a partial or total obliteration of clinical symptoms of allergic response due to exposure to a given allergen(s). Administration may be by any suitable route and will vary according to the allergen, the individual, and the desired clinical results. MLA or 3D-MLA may be administered through mucosal surfaces such as orally, intranasally or by inhalation. Parenteral routes, i.e., intraperitoneal or intramuscular, while less preferred, may be used. The preferred route of administration is subcutaneously.

The precise dosage will depend upon the particular MLA or 3D-MLA used, the route of administration, the pharmaceutical composition, and the patient. For example, when the most preferred route of administration (subcutaneous) is utilized, the amount of active ingredient (MLA or 3D-MLA) is from 1 to about 250 micrograms, preferably from about 25 to about 50 micrograms based upon administration to a typical 70 kg adult patient.

The method of the present invention contemplates single or multiple doses, depending upon the particular situation. The preferred route of administration and dosage regimes for a given case may be ascertained by relatively routine experimentation involving clinical trials.

The term "pharmaceutically acceptable carrier" as used in this description means a medium which does not interfere with the medicinal activity of the active ingredient and is not toxic to the patient to whom it is administered. Pharmaceutically acceptable carriers include oil-in-water or water-in-oil emulsions, aqueous compositions, liposomes, microbeads, microsomes or alum.

Examples of preferred carriers for subcutaneous use include a phosphate buffered saline (PBS) solution and 0.01–0.1% triethanolamine in USP Water for Injection. One point worthy of mention with regard to the carrier is that it has been found, so far, that normal saline solution cannot be used with the active components of the present invention since MLA and 3D-MLA precipitate out in normal saline solution. Pharmaceutically acceptable parenteral solvents are such as to provide a solution or dispersion of the active ingredients of the present invention such that the solution or dispersion may be filtered through a 5 micron filter without removing the active ingredient.

Carriers for intramuscular use include 10% USP ethanol, 40% glycol propylene and the balance an acceptable isotonic solution such as 5% dextrose. MLA or 3D-MLA entrapped in liposomes could alternatively be further solubilized for intramuscular use in normal saline, as precipitation of the active ingredient will not occur in saline when the solubility of MLA or 3D-MLA is stabilized in liposomes.

Examples of carriers for administration via mucosal surfaces depend upon the particular route. When administered orally, pharmaceutical grades of mannitol, starch, lactose, magnesium stearate, sodium saccharide, cellulose, magnesium carbonate and the like may be used, with mannitol being preferred. When administered intranasally, polyethylene glycol or glycols, sucrose, and/or methylcellulose, and preservatives such as benzalkonium chloride, EDTA, may be used, with polyethylene glycols being preferred, and when administered by inhalation, suitable carriers are polyethylene glycol or glycols, methylcellulose, dispensing agents, and preservatives, with polyethylene glycols being preferred.

MLA or 3D-MLA may be administered in a suitable vehicle alone or co-administered with other active components. For example, in a preferred embodiment, MLA or 3D-MLA can be administered with an allergen as part of a desensitization regimen. The precise schedule of co-administration will depend upon the patient, the severity of his or her hypersensitivity, and the route of administration. Generally, the treating physician designs a regimen based upon these factors, and the regimen is finally determined by relatively routine experimentation to achieve the desired results.

When a composition containing MLA or 3D-MLA is co-administered with an allergen(s) to treat type I hypersensitivity as part of a desensitization regimen, such composition may be administered from twenty-four hours before to twenty-four hours after administration of the allergen(s), and preferably from one hour prior, to concurrent with the administration of the allergen(s).

An "allergen" is any substance which can elicit a type I hypersensitive response. Typical allergens include, but are not limited to, pollens, molds, foods, animal danders or their excretions, smuts and insects, their venoms or their excretions. They may be administered singly or as a mixture depending upon the nature of the type I hypersensitivity. The allergens may be chemically or physically modified. Such modified allergens, or allergen derivatives, are known in the art. Examples include, but are not limited to, peptide fragments, conjugates or polymerized allergen derivatives.

The amount of allergen to be administered can be determined empirically and depends on the sensitivity of the individual as well as the desired clinical result. Generally, a regimen of desensitization initially involves the periodic administration of smaller amounts of allergen, which level is increased over the course of the regimen until a predetermined (planned) upper limit is reached or the individual can tolerate exposure to such allergen without a significant adverse allergic response. The particular regimen often is tailored to individual patient needs. The embodiment and potential advantage of the present invention is that it may be possible to meaningfully decrease the level of allergens administered and/or the number of injections and, thereby, the length of the desensitization regimen. Further, with a meaningful decrease of the level (dose) of allergen administered to particularly sensitive individuals, there is a possible diminished risk of severe allergic reaction to the administration of the allergen.

The progress of immunotherapy can be monitored by any clinically acceptable diagnostic tests. Such tests are well known in the art and include symptom levels and requirement levels for ancillary therapy recorded in a daily diary, as well as skin testing and in vitro serological tests for specific IgE antibody and/or specific IgG antibody.

The following examples are offered to further illustrate but not limit both the compositions and the method of the present invention. It is to be understood that the rat and mouse models presented herein are representative of warm blooded animals and correlate reasonably with events for other warm blooded animals, including humans.

EXAMPLE I

This example demonstrates the activity of 3D-MLA in reducing the level of IgE in a model designed to induce an IgE response.

BALB/c or C57B1/6 mice were immunized subcutaneously with 100 µg Ovalbumin (OVA) (from Sigma Chemical)+1 µg Pertussis toxin (PT) (from Research Products Intl.) in 2% oil-in-water emulsion±50 µg 3D-MLA. They were given a boost immunization at day 14 after the primary immunization. Mice were bled at various times and sera quantitated for total IgE by ELISA (reagents from Southern Biotechnology Assn., Inc.) using a standard curve for mouse IgE.

With reference to Table 1 below, the data show a significant decrease in total IgE sera levels when 3D-MLA is co-administered with an Ovalbumin allergen.

TABLE 1

| | | Total IgE (ng/ml) | | |
|---|---|---|---|---|
| | Mouse Strain | Day 6 - post 1° | Day 13 - post 1° | Day 10 - post 2° |
| OVA + PT | BALB/c | 400 | 475 | 750 |
| | | (−68%) | (−89%) | (−91%) |
| OVA + PT + 3D-MLA | BALB/c | 125 | 50 | 65 |
| OVA + PT | C57B1/6 | 260 | 250 | 300 |
| | | (−52%) | (−60%) | (−85%) |
| OVA + PT + 3D-MLA | C57B1/6 | 125 | 100 | 45 |

EXAMPLE II

This example demonstrates the activity of 3D-MLA in reducing total sera IgE levels elaborated by a house dust allergen in a mouse model.

BALB/c or C57B1/6 mice were immunized subcutaneously with 100 µg house dust allergen (HDA)+1 pg Pertussis toxin (PT) in 2% oil-in-water emulsion+50 µg 3D-MLA. On day 14 after the primary immunization the mice were given a boost immunization. Mice were bled 10 days after the boost immunization and the total IgE quantitated by ELISA using a standard curve for mouse IgE.

As can be seen with reference to Table 2 below, consistent with the results achieved in the previous experiment, and utilizing a different allergen, the results show a significant decrease in total IgE sera levels when 3D-MLA is co-administered with a house dust allergen.

TABLE 2

| | Total IgE (ng/ml) ± SE | |
|---|---|---|
| | Mouse Strain | Day 10 - post 2° |
| HDA + PT | BALB/c | 450 ± 72 |
| | | (−69%) |
| HDA + PT + 3D-MLA | BALB/c | 140 ± 40 |
| HDA + PT | C57B1/6 | 1,250 ± 201 |
| | | (−64%) |
| HDA + PT + 3D-MLA | C57B1/6 | 450 ± 27 |

EXAMPLE III

This example demonstrates the effect of 3D-MLA on allergen specific IgE levels in response to multiple dosing with low levels of allergen.

Brown Norway (high IgE responding) rats (150–200 g; 5 animals per group) were prebled and immunized with 10 µg Keyhole Limpet Hemocyanin (KLH) (from Sigma Chemical). KLH was alum precipitated and mixed with $10^9$ killed *Bordetella pertussis* organisms (from Connaught Laboratories). Group A was treated subcutaneously with 30 µg KLH in saline on day 14, 21, 28 and 35, with 200 µg 3D-MLA in 0.2 ml 0.5% triethanolamine, which was subsequently administered close to the subcutaneous site on days 15, 22, 29 and 36. Group B was treated as Group A, except that 0.5% triethanolamine diluent replaced the 3D-MLA preparation as a control. All animals were bled on days 14, 28 and 42. Specific IgE was measured by PRAST assay, with KLH as disc coating antigen. Bound IgE was detected by monoclonal $^{125}$I mouse anti-rat IgE (MARE-1). The results are shown in Table 3.

On day 42 the data show a significant difference in the allergen-specific response between animals receiving 3D-MLA (Group A) and the controls which did not receive 3D-MLA (Group B). Animals not receiving 3D-MLA displayed a steady increase in levels of antigen-specific IgE with each injection of KLH. IgE levels in animals receiving 3D-MLA did not increase with subsequent injections of KLH. These results indicate that the administration of 3D-MLA prevents the increase of antigen-specific IgE upon repeated exposure to allergen.

TABLE 3

| Drug | Day 14 | Day 28 | *Day 42 |
| --- | --- | --- | --- |
| 3D-MLA | 14 ± 2.0 | 11.5 ± 2.0 | 11.0 ± 2.0 |
| Control | 22 ± 2.5 | 35 ± 16.0 | 44 ± 1.5 |

Numbers represent number of anti-KLH IgE antibody units/ml with standard of error of mean.
*p value of <0.05

EXAMPLE IV

MLA can be administered in the same quantities and amounts as 3D-MLA in Examples I–III to produce similar results.

From the foregoing examples, it can be seen that the compositions and methods embodied by the present invention are effective to significantly reduce the level of IgE antibody associated with type I hypersensitivity in response to exposure to allergen(s) and are further effective to stimulate the production of blocking IgG antibodies, thereby reducing the risks and severity of allergic reactions upon exposure to the allergen(s) to which the patient suffers hypersensitivity.

It is understood that the foregoing examples are illustrative of the present invention and are not intended to include all possible variations thereof. Certain modifications of the compositions and/or methods employed may be made and still achieve the objectives of the invention. Such modifications are contemplated as within the scope of the claimed invention.

What is claimed is:

1. A method of treating type I hypersensitivity in a warm blooded animal sensitive to an allergen which comprises administering to the warm blooded animal a pharmaceutical composition comprising an effective amount of a refined detoxified endotoxin selected from the group consisting of monophosphoryl lipid A and 3-deacylated monophosphoryl lipid A, a pharmaceutically acceptable carrier, and at least one allergen to which the warm blooded animal is sensitive.

2. The method of claim 1, wherein said refined detoxified endotoxin is administered in an amount from about 1.0 microgram to about 250 micrograms.

3. The method of claim 1, wherein said refined detoxified endotoxin is administered in an amount from about 25 micrograms to about 50 micrograms.

4. The method of claim 1 wherein said refined detoxified endotoxin is monophosphoryl lipid A.

5. The method of claim 1, wherein said refined detoxified endotoxin is 3deacylated monophosphoryl lipid A.

6. The method of claim 1, wherein said pharmaceutical composition is administered orally.

7. The method of claim 1, wherein said pharmaceutical composition is administered parenterally.

8. The method of claim 1, wherein said pharmaceutical composition is administered subcutaneously.

9. The method of claim 1, wherein said pharmaceutical composition is administered from about one hour prior to about one hour after the administration of said allergen.

10. The method of claim 1, wherein said pharmaceutical composition is administered concurrently with the administration of said allergen.

11. The method of claim 1, wherein said allergen is selected from the group consisting of pollen allergen, mold allergen, insect venom allergen, insect saliva allergen, insect part allergen, insect excreta allergen, animal dander allergen, animal excreta allergen, drug allergen, chemical allergen and food allergen.

12. A method of reducing IgE antibody and increasing IgG antibody in a warm blooded animal, which method comprises administering to the warm blooded animal a pharmaceutical composition comprising an effective amount of a refined detoxified endotoxin selected from the group consisting of monophosphoryl lipid A and 3-deacylated monophosphoryl lipid A, a pharmaceutically acceptable carrier, and a compound selected from the group consisting of an allergen, a bacterial antigen, a viral antigen and a microbial antigen.

13. The method of claim 12, wherein said refined detoxified endotoxin is administered in an amount from about 1.0 microgram to about 250 micrograms.

14. The method of claim 12, wherein said refined detoxified endotoxin is administered in an amount from about 25 micrograms to about 50 micrograms.

15. A pharmaceutical composition for treating type I hypersensitivity in a warm blooded animal sensitive to an allergen comprising an effective amount of a refined detoxified endotoxin selected from the group consisting of monophosphoryl lipid A and 3-deacylated monophosphoryl lipid A, an effective amount of an allergen to which said warm blooded animal is sensitive and a pharmaceutically acceptable carrier.

16. The pharmaceutical composition of claim 15, wherein said refined detoxified endotoxin is monophosphoryl lipid A.

17. The pharmaceutical composition of claim 15, wherein said refined detoxified endotoxin is 3-deacylated monophosphoryl lipid A.

* * * * *